(12) United States Patent
Firmbach et al.

(10) Patent No.: US 12,343,020 B2
(45) Date of Patent: Jul. 1, 2025

(54) SURGICAL INSTRUMENT SYSTEM

(71) Applicant: Aesculap AG, Tuttlingen (DE)

(72) Inventors: Franz-Peter Firmbach,
Emmingen-Liptingen (DE); Svenja Anhorn, Heroldstatt (DE)

(73) Assignee: Aesculap AG, Tuttlingen (DE)

( * ) Notice: Subject to any disclaimer, the term of this patent is extended or adjusted under 35 U.S.C. 154(b) by 289 days.

(21) Appl. No.: 18/321,963

(22) Filed: May 23, 2023

(65) Prior Publication Data
US 2023/0380845 A1      Nov. 30, 2023

(30) Foreign Application Priority Data

May 24, 2022   (DE) .................... 10 2022 205 193.9

(51) Int. Cl.
*A61B 17/15*      (2006.01)

(52) U.S. Cl.
CPC ................................. *A61B 17/155* (2013.01)

(58) Field of Classification Search
CPC .................................................. A61B 17/155
See application file for complete search history.

(56) References Cited

U.S. PATENT DOCUMENTS

| 5,662,656 A | 9/1997 | White |
| 5,676,668 A | 10/1997 | Mccue et al. |
| 5,683,397 A * | 11/1997 | Vendrely ............ A61B 17/155 606/88 |
| 10,130,375 B2 | 11/2018 | Yager et al. |
| 2004/0153084 A1 | 8/2004 | Haney et al. |
| 2011/0060340 A1 | 3/2011 | Dees, Jr. et al. |
| 2016/0030053 A1 | 2/2016 | Yager et al. |
| 2017/0348009 A1 | 12/2017 | Dmuschewsky |
| 2021/0236143 A1 | 8/2021 | Shah |

FOREIGN PATENT DOCUMENTS

| DE | 4339895 C1 | 3/1995 |
| DE | 69722052 T2 | 4/2004 |
| DE | 69636636 T2 | 8/2007 |
| DE | 102015100049 A1 | 7/2016 |
| WO | 9514444 A1 | 6/1995 |
| WO | 9721390 A1 | 6/1997 |
| WO | 9920192 A1 | 4/1999 |
| WO | 2018216026 A1 | 11/2018 |

\* cited by examiner

*Primary Examiner* — Samuel S Hanna
(74) *Attorney, Agent, or Firm* — Christopher A. Rothe; CM Law

(57) ABSTRACT

A surgical instrument system for use in a total knee arthroplasty includes an intramedullary rod and a reference block. The intramedullary rod is elongated between a proximal rod end and a distal rod end and is adapted for introduction into the medullary space of a femur. The reference block is or can be slid onto the distal rod end and has a block rear side oriented in a proximal direction. The block rear side is adapted to bear on distal condyles of the femur. The reference block is mounted to or mountable on the distal rod end by a bearing element having a reception bore for coaxial and radially form-fit reception of the distal rod end. The bearing element is mounted on the reference block so as to be pivotable relative thereto at least about a pivot axis oriented in an anteroposterior direction.

8 Claims, 8 Drawing Sheets

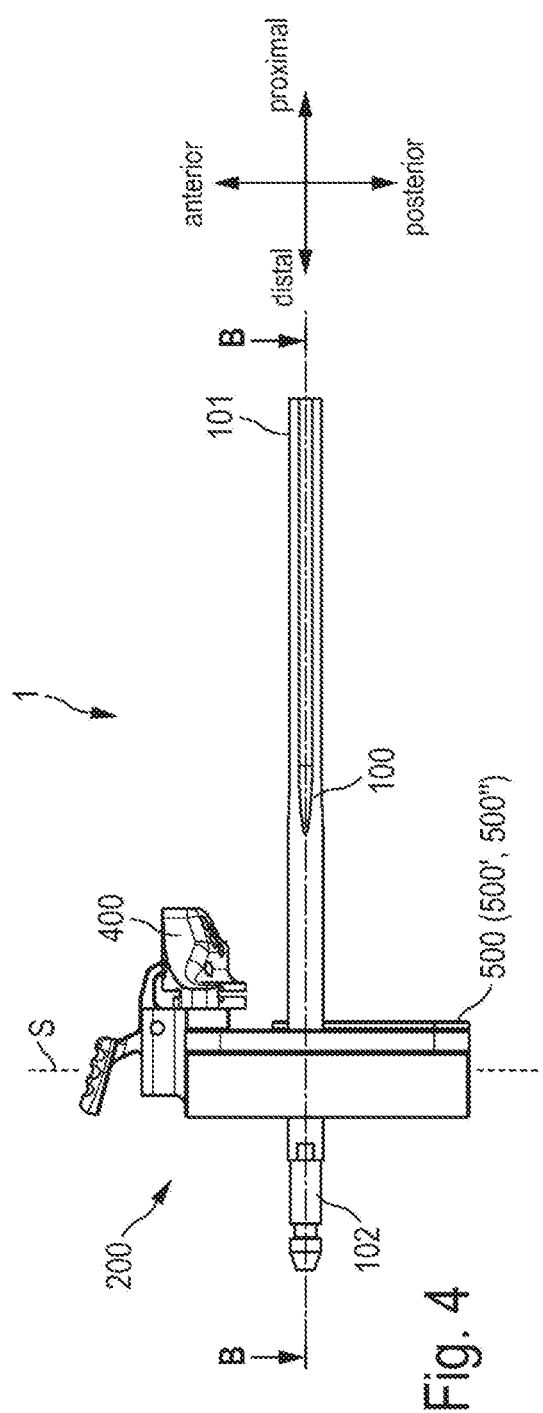
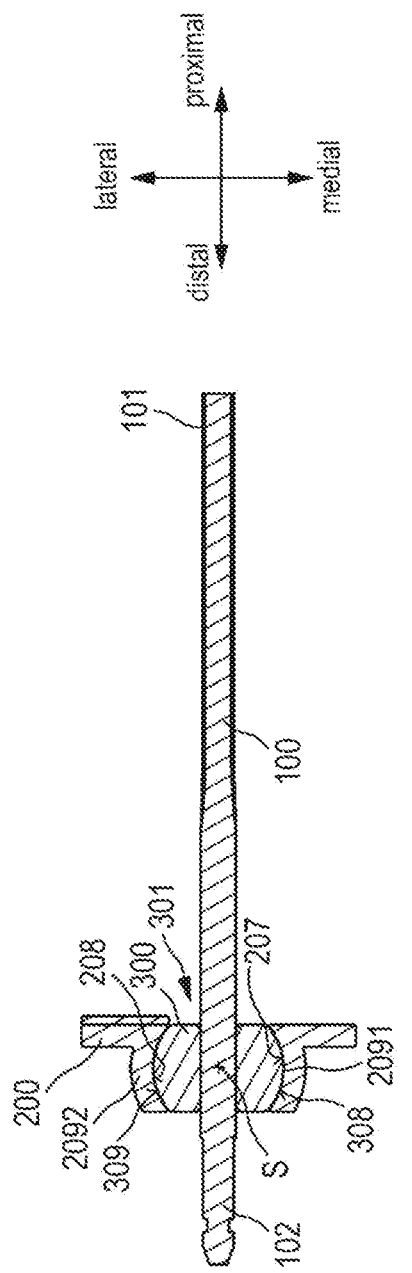
Fig. 4
Fig. 5

__SURGICAL INSTRUMENT SYSTEM__

CROSS-REFERENCE TO RELATED APPLICATION(S)

This application claims priority under 35 U.S.C. § 119 to German Application No. 10 2022 205 193.9, filed on May 24, 2022, the content of which is incorporated by reference herein in its entirety.

FIELD

The present disclosure relates to a surgical instrument system for use in a total knee arthroplasty, having an intramedullary rod which is elongated between a proximal rod end and a distal rod end and is adapted for introduction into the medullary space of a femur, and having a reference block, which is or can be slid onto the distal rod end and has a block rear side oriented in a proximal direction, which is adapted to bear on distal condyles of the femur.

BACKGROUND

The use of orthopaedic prostheses as an artificial replacement for damaged or worn natural bone structures of a patient is common medical practice. In particular, total hip and knee arthroplasties belong to the standard repertoire of surgical orthopaedics.

In a total knee arthroplasty (TKA), articular surfaces of the femur and/or tibia that are worn or affected in some other way by disease or an accident are replaced with a knee joint prosthesis. Such knee joint prostheses conventionally comprise a femoral component, which is implanted at the distal end of the femur, and a tibial component, which is implanted at the proximal end of the tibia. In order to ensure an unimpaired function of the artificial joint replacement, said components need to be positioned as precisely as possible in a defined way with regard to their location and orientation in relation to the anatomy of the patient and the patient's body axes. Otherwise, an unsatisfactory outcome may be expected for the patient. With regard to the positioning of the components, there are different surgical approaches.

According to one approach, which is known as mechanical alignment and has long been conventional, the position and alignment of the artificial articular axes of the knee joint prosthesis are mechanically aligned ideally, and to this extent without taking into account any orthopaedic deformities of the patient. In this case, the longitudinal axis of the tibia is often used as a reference axis for the alignment and positioning. Clinical studies have shown that the mechanical alignment approach may lead to a function of the artificial knee joint that is felt to be unnatural.

As another approach, so-called kinematic alignment is known. In this procedure, the femoral component and the tibial component are positioned while taking into account any orthopaedic deformities of the patient. The aim is in this case to reproduce the patient's natural articular alignment, which may sometimes be affected by deformities. Clinical studies have shown that the kinematic alignment approach is often associated with an improved patient satisfaction. In particular, the function of the artificial knee joint is felt to be more natural by the patient.

With the desire to further improve patient satisfaction, there is a fundamental need for surgical instruments and instrument systems for carrying out kinematic alignment, which are as precise, easy to use and cost-efficient as possible.

One example of a surgical instrument system, which has an intramedullary rod and a reference block, is known from U.S. Pat. No. 10,130,375 B2. The intramedullary rod is elongated between a proximal rod end and a distal rod end and is adapted for introduction into the medullary space of a femur. The reference block has a block rear side oriented in a proximal direction, which is adapted to bear on distal condyles of the femur. The reference block furthermore has a fixing device for the releasable fixing of a distal femoral cutting block. For positioning on the femoral side, the reference block can be slid starting from the distal rod end in a proximal direction onto the intramedullary rod. For this purpose, the reference block of the known surgical instrument system has a longitudinal hole. The longitudinal hole extends axially between the block rear side and a block front side lying opposite in a distal direction and is elongatedly extended in a mediolateral direction. As a result, the reference block is relatively movable in a limited manner in a mediolateral direction when it is slid on. The reference block is furthermore tiltable relative to the intramedullary rod about a tilt axis oriented in an anteroposterior direction, a position of the tilt axis in relation to the intramedullary rod received in the longitudinal hole not being uniquely defined and being variable within fixed limits.

SUMMARY

It is an object of the present disclosure to provide a surgical instrument system of the type mentioned in the introduction, which allows precise adjustment of the location and orientation of the reference block and ultimately improved operation outcomes.

The present disclosure relates to such surgical instrument systems, in particular a surgical instrument system for positioning a distal femoral cutting block in the scope of kinematic alignment.

This object is achieved in that the reference block is mounted or mountable by means of a bearing element on the distal rod end, the bearing element having a reception bore for coaxial and radially form-fit reception of the distal rod end and being mounted on the reference block so as to be pivotable relative thereto at least about a pivot axis oriented in an anteroposterior direction. The solution according to the present disclosure achieves improved mounting of the reference block on the intramedullary rod. In comparison with the solutions known from the prior art, the present disclosure allows kinematically well-defined relative mobility of the reference block. This way, the location and orientation of the reference block can be adjusted precisely. In particular, by the pivotability of the reference block about the pivot axis oriented in an anteroposterior direction, the *varus*-valgus angle can be adjusted precisely. In this way, misalignments of the kinematic axes of the knee joint replacement can be avoided and improved operation outcomes are made possible. The reference block is mounted or mountable indirectly, specifically by means of the bearing element, on the intramedullary rod. For this purpose, the bearing element has said reception bore. The reception bore is configured dimensionally complementarily to the intramedullary rod. When the reference block is slid on, the reception bore and the intramedullary rod are aligned coaxially to one another and the intramedullary rod is received in the reception bore with a form fit in a radial direction. Because of the form fit, the bearing element and the intramedullary rod are secured relative to one another in both a mediolateral and anteroposterior direction. The pivotability of the reference block in relation to the intramedullary rod is made possible by the pivotable mounting of the bearing element on the reference block. The mounting may for example be configured as gliding guiding, axial guiding or the like, and may comprise component parts and/or sections that are arranged and/or formed on the one hand on the reference block and on the other hand on the bearing element.

The positional and directional terminology used in this description refer to the body of a patient, in particular the patient's femur, and to this extent are to be understood according to their conventional anatomical meaning. Consequently, "anterior" means front or lying at the front, "posterior" means rear or lying at the rear, "medial" means inner or lying inwards, "lateral" means outer or lying outwards, "proximal" means towards the centre of the body and "distal" means away from the centre of the body. Furthermore, "proximodistal" means along, preferably parallel to, an axis aligned in a proximal-distal direction, "anteroposterior" means along, preferably parallel to, an axis aligned in an anterior-posterior direction and "mediolateral" means along, preferably parallel to, an axis aligned in a medial-lateral direction. Said axes are aligned orthogonally to one another and may, of course, be set in relation to X, Y and Z axes that are not connected with the anatomy of the patient. For example, the proximal-distal axis may alternatively be referred to as the X axis. The medial-lateral axis may be referred to as the Y axis. The anterior-posterior axis may be referred to as the Z axis. For improved illustration and for the sake of simplicity of the terminology, said anatomical positional and directional terminology will primarily be used below. Furthermore, terms such as "rear side" of a component or a section of the surgical instrument system, for example of the reference block, will be used in relation to a proximally directed viewing direction. Conversely, terms such as "front side" will be used in relation to a distally directed viewing direction.

In one embodiment of the present disclosure, the reference block has a gliding guide with guide faces that are concavely curved in the shape of a circle arc and lie opposite one another in a mediolateral direction, and the bearing element has gliding faces that are convexly curved in the shape of a circle arc and lie opposite one another in a mediolateral direction, the gliding faces being able to glide in rotation about the pivot axis and cooperating with the guide faces form-fittingly in a proximodistal and mediolateral direction. In this way, pivotable mounting that is particularly simple in terms of design but nevertheless precise and robust is achieved between the bearing element and the reference block. The guide faces and the gliding faces are each in the shape of a circle arc in relation to an anteriorly or posteriorly directed viewing direction. The guide faces and the gliding faces are curved complementarily to one another, the guide faces being concave and the gliding faces respectively being convex. The guide faces define an inner diameter of the gliding guide. The gliding faces define a complementary outer diameter. The outer diameter fits into the inner diameter. The fit is preferably selected in such a way that a precise relative mobility which is free of play and at the same time sufficiently smooth is achieved between the bearing element and the reference block. Preferably, the reception bore is arranged in a mediolateral direction, preferably centrally, between the opposing gliding faces of the bearing element. The opposing guide faces may also be referred to as a first guide face and second guide face, or alternatively as a medial guide face and lateral guide face. The same applies, mutatis mutandis, with regard to the gliding faces.

In another embodiment of the present disclosure, the guide faces are each rectilinearly elongated parallel to the pivot axis, the gliding faces cooperating along the pivot axis in translational movement with the guide faces. In this way, the reference block is able to glide in an anteroposterior direction relative to the intramedullary rod. This allows adjustment of the anteroposterior position of the reference block. In this way, the positioning of the reference block can be adapted in an improved way to a given size of the femur. Because of their rectilinear elongation, the opposing guide faces each substantially form a guide path. The reference block is displaceable in translation along the pivot axis and/or the guide path between an upper end location and a lower end location relative to the bearing element.

In another embodiment of the present disclosure, the reference block has a reception slot, which reaches from the block rear side onto a block front side lying opposite in a distal direction and is rectilinearly elongated parallel to the pivot axis and has inner walls, which lie opposite one another in a mediolateral direction and on which the guide faces are arranged and/or formed, the reception slot having an insertion opening arranged anteriorly on a block upper side or posteriorly on a block lower side of the reference block for insertion of the bearing element. The reception slot allows particularly simple and time-saving application of the bearing element on the reference block, or vice versa. For example, the bearing element may initially be slid with the reception bore foremost in a proximal direction onto the distal rod end. The reference block may subsequently be slid along the pivot axis in an anterior or posterior direction, depending on whether the insertion opening is arranged on the (anterior) block upper side or (posterior) lower side, onto the bearing element. Alternatively, the bearing element may be introduced into the reception slot before being slid onto the intramedullary rod. In one embodiment, the insertion opening is arranged on the block upper side of the reference block. In another embodiment, the insertion opening is arranged on the block lower side. The block upper side and the block lower side lie opposite one another in an anteroposterior direction. Preferably, the reception slot subdivides the reference block into a lateral block section and a medial block section. A rear side of the medial block section is adapted to bear on the medial distal condyle of the femur. A rear side of the lateral block section is adapted to bear on the lateral distal condyle of the femur.

In another embodiment of the present disclosure, the reference block has an axial guide with at least one axial element oriented coaxially with the pivot axis, and the bearing element has at least one axial recess oriented coaxially with the pivot axis, the axial element engaging in the axial recess in such a way that it can glide about the pivot axis. The axial element is preferably configured as a pin, bolt and/or peg, so that the terms axial pin, axial bolt or axial peg may also be used. The axial guide is constructed relatively simply in terms of design. This allows simple production and assembly, as well as associated cost savings. At the same time, however, sufficiently precise pivotable mounting can be achieved. In one embodiment, the reference block has two axial elements and the bearing element correspondingly has two axial recesses, each of which cooperates with one of the axial elements. In this context, the terms anterior axial element and posterior axial element may also be used. The same applies, mutatis mutandis, with regard to the axial recesses. In said embodiment, the reception bore is preferably arranged in an anteroposterior direction, preferably centrally, between the anterior axial recess and the posterior axial recess.

In another embodiment of the present disclosure, the at least one bearing element is mounted releasably on the reference block, and a plurality of different bearing elements having differently inclined elongated reception bores are provided, which can be mounted mutually interchangeably on the reference block in order to adjust an inclination angle of the latter. The plurality of different bearing elements preferably differ from one another only with regard to the inclination of the reception bore. Preferably, the different bearing elements are in other regards identical. Because of the differently inclined elongated reception bores, the inclination angle of the reference block can be adjusted in a simple and precise way—by a corresponding selection of the respective bearing element. Preferably, the reception bores are inclined differently in relation to the proximally oriented block rear side of the reference block. The reception bores are in this case preferably inclined differently relative to the normal direction of the block rear side in an anterior direction and/or posterior direction. This allows simple and precise adjustment of the flexion-extension angle of the reference block, that is to say its angle of rotation about an axis aligned in a mediolateral direction.

In another embodiment of the present disclosure, a plurality of different compensation elements having different proximodistal thicknesses are provided, which can be applied mutually interchangeably on the block rear side in order to compensate for a differently pronounced wearing of the posterior condyles. As mentioned in the introduction, the surgical instrument system is intended for implementation of the kinematic alignment approach. This approach conventionally provides dimensional compensation for the condylar wear. For this purpose, in this embodiment of the present disclosure the surgical instrument system has a plurality of different compensation elements having a different proximodistal thickness, which can be interchanged with one another.

In another embodiment of the present disclosure, a cutting block is provided, which is adapted for cut guiding on the distal condyles of the femur and is releasably fixed or fixable on a fixing device of the reference block. The cutting block may also be referred to as a sawing block or cutting jig. The cutting block has at least one guide slot for receiving and guiding a saw blade. The basic configuration and functionality of such a cutting block are known to a person skilled in the art. The fixing device is preferably arranged in the region of the anterior block upper side of the reference block.

In another embodiment of the present disclosure, the intramedullary rod has a length of between 120 mm and 250 mm, preferably between 150 mm and 220 mm, particularly preferably between 170 mm and 200 mm.

BRIEF DESCRIPTION OF THE DRAWINGS

Further advantages and features of the present disclosure may be found in the following description of preferred exemplary embodiments of the present disclosure, which are represented with the aid of the drawings.

FIG. 4 shows the surgical instrument system according to FIG. 1 in a schematic side view with a laterally directed viewing direction.

FIG. 5 shows a schematic longitudinal sectional view along a section line B-B according to FIG. 4.

DETAILED DESCRIPTION

Figure 1:
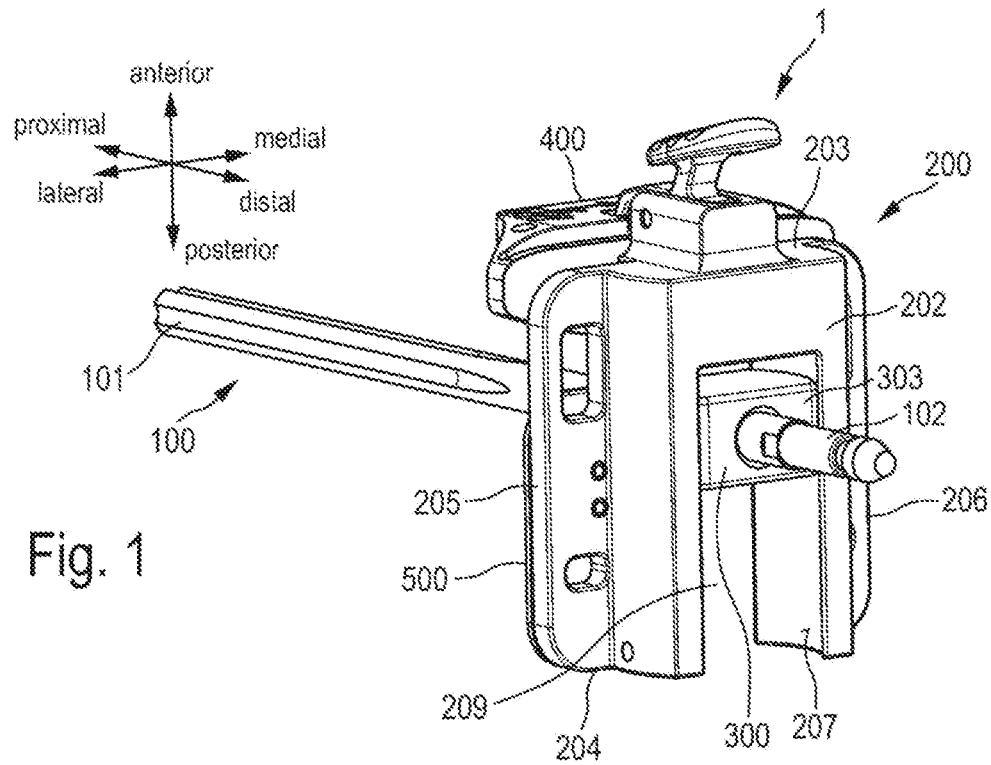
FIG. 1 shows a schematic perspective view of one embodiment of a surgical instrument system according to the present disclosure having an intramedullary rod, a reference block, a bearing element and a cutting block.

According to FIGS. 1 to 7, a surgical instrument system 1 for use in a total knee arthroplasty is provided, which has an intramedullary rod 100, a reference block 200, at least one bearing element 300, a cutting block 400 and at least one compensation element 500.

Figure 3:
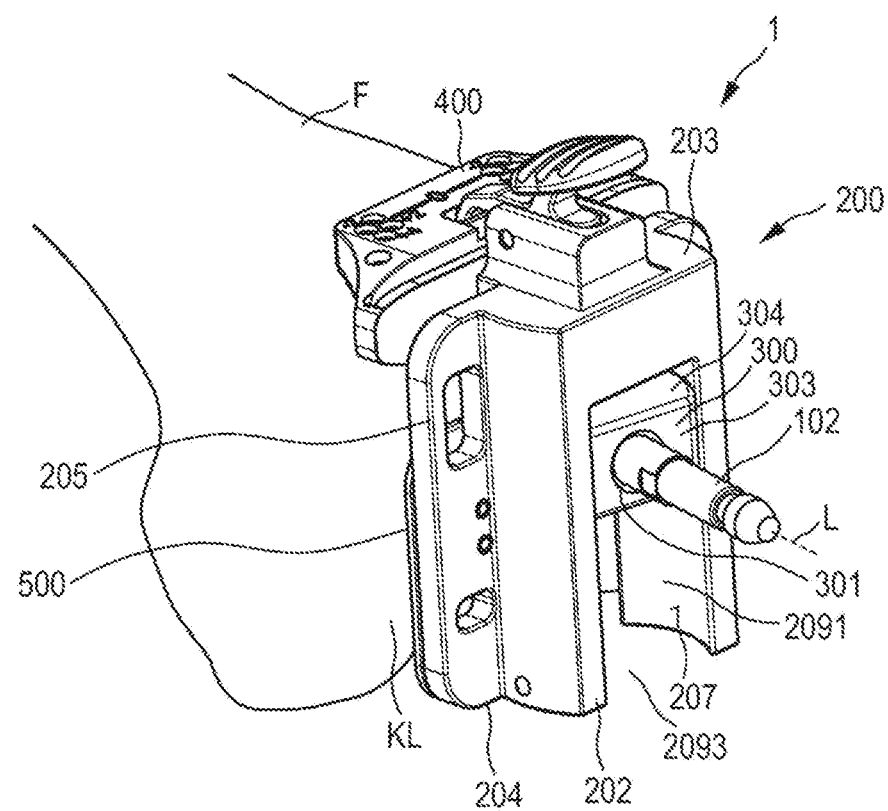
FIG. 3 shows a schematic perspective view of an intraoperative situation when using the surgical instrument system according to FIG. 1.

The intramedullary rod 100 is rectilinearly elongated between a proximal rod end 101 and a distal rod end 102, and is adapted for introduction into a medullary space of a femur F (see FIG. 3). The intramedullary rod 100 (abbreviated below to: rod) is aligned during use coaxially with a proximodistal longitudinal axis of the femur F. During use, the distal rod end 102 protrudes from the femur F at the end and projects beyond the distal condyles of the latter, only a lateral distal condyle KL of the femur F being visible in FIG. 3.

The reference block 200 can be slid onto the rod 100 in an axial direction of the latter. The reference block 200 has a block rear side 201, a block front side 202, a block upper side 203, a block lower side 204 and block outer sides 205, 206. The block rear side 201 is oriented in a proximal direction. That is to say, a surface normal (without reference sign) of the block rear side 201 is aligned along a proximodistal axis (FIG. 1), the alignment not necessarily having to be parallel as will be explained in more detail below. The block front side 202 lies opposite the block rear side 201 in a distal direction. The block upper side 203 is arranged in an anterior direction on the reference block 200. The block lower side 204 lies opposite the block upper side 203 in a posterior direction. The two block outer sides 205, 206 lie opposite one another in a mediolateral direction, and may also be referred to as a lateral block outer side 205 and a medial block outer side 206.

The proximally oriented block rear side 201 is adapted to bear on the said distal condyles of the femur F (see FIG. 3). The reference block 200 is mounted by means of the bearing element 300 on the distal rod end 102.

For this purpose the bearing element 300 has a reception bore 301, which is adapted for coaxial and radially form-fit reception of the distal rod end 102. Furthermore, the bearing element 300 is mounted on the reference block 200 so as to be able to pivot relative to the reference block 200 at least about a pivot axis S oriented in an anteroposterior direction.

The bearing element 300 has a proximally oriented rear side 302, a front side 303 lying opposite in a distal direction, an anteriorly oriented upper side 304, a lower side 305 lying opposite in a posterior direction, and outer sides 306, 307 which lie opposite one another in a mediolateral direction. The latter may also be referred to as a lateral outer side 306 and a medial outer side 307. The reception bore 301 is elongated along a longitudinal axis L (see FIG. 8) between the rear side 302 and the front side 303. The longitudinal axis L and the pivot axis S are aligned orthogonally to one another in the case of the bearing element 300. As will be described in more detail below, alignments differing therefrom are also provided.

An outer circumference (without reference sign) of the rod 100 and the reception bore 301 cooperate substantially without play with a form fit in a radial direction of the reception bore 301. In an axial direction of the reception bore 301, that is to say along the longitudinal axis L and therefore also along the proximodistal axis, the bearing element 300 can move by gliding relative to the rod 100. Furthermore, the bearing element 300 is fundamentally rotatable in a circumferential direction of the rod 100 about the longitudinal axis L. Apart from this, no relative movement is possible between the bearing element 300 and the rod 100.

Because of the pivotable mounting between the reference block 200 and the bearing element 300, the reference block 200 can be positioned in different angular positions about the pivot axis S relative to the rod 100 and therefore also relative to the femur F. This allows simple and precise adjustment of the *varus*-valgus angle for the distal resection of the femur F which is subsequently to be carried out by means of the cutting block 500.

The pivot axis S intersects the longitudinal axis L of the reception bore 301 and therefore also the longitudinal axis (without separate reference sign) of the rod 100.

In the embodiment according to FIGS. 1 to 7, for the purpose of pivotable mounting there is a gliding guide having guide faces 207, 208 and gliding faces 308, 309 (see in particular FIG. 5).

In the present case, the reference block 200 has the guide faces 207, 208. The bearing element, on the other hand, has the gliding faces 308, 309.

The guide faces 207, 208 lie opposite one another in a mediolateral direction and are each—in relation to an anteriorly or posteriorly directed viewing direction (see FIG. 5)—concavely curved in the shape of a circle arc. The gliding faces 308, 309 are shaped complementarily to the guide faces 207, 208. Accordingly, the gliding faces 308, 309 are arranged opposite one another in a mediolateral direction on the bearing element 300 and are convexly curved in the shape of a circle arc. The gliding faces 308, 309 cooperate with the guide faces 207, 208 in rotational gliding movement about the pivot axis S. The said faces 207, 307, 208, 308 cooperate with a form fit in a proximodistal direction, and therefore along the longitudinal axis L. There is furthermore a form fit in a mediolateral direction.

The guide faces 207, 208 may also be referred to as a medial guide face 207 and lateral guide face 208. Expressed in other words, the medial guide face 207 lies on a medial side of the pivot axis S and/or of the rod 100. The lateral guide face 208, on the other hand, lies on a lateral side of the pivot axis and/or of the rod 100. The gliding faces 308, 309 may also be referred to as a medial gliding face 308 and lateral gliding face 309. The medial gliding face 308 is arranged on the medial outer side 307 or is formed thereby. Here, the latter is the case. The lateral gliding face 309 is formed by the lateral outer side 306.

In the present case, the guide faces 207, 208 are each rectilinearly elongated parallel to the pivot axis S. Because of the rectilinear and parallel lengthwise extent, the guide faces 207, 208 form, so to speak, a guide path E extending along the pivot axis S (see in particular FIG. 2). The reference block 200 and the bearing element 300 are displaceable relative to one another in translation along the guide path E. In this way, the reference block 200 can be positioned in different positions in relation to the anteroposterior axis relative to the rod 100, and therefore also relative to the femur F. In other words, the reference block 200 can be positioned differently in relation to its height axis (not denoted in detail) on the distal femur F. In this way, the position of the reference block 200 can be adapted simply and precisely to femoral bones of different size. As is shown with the aid of FIG. 3, the reference block 200 is displaceable along the guide path E (FIG. 2) relative to the bearing element 300 between a lower end location and an upper end location. In FIG. 3, for example, positioning in the region of the lower end location is shown. The upper end location is occupied when the reference block 200 is displaced starting from the position shown in FIG. 3 upwards in relation to the plane of the drawing until it reaches a lower end of the guide faces 207, 208.

In the present case, the reference block 200 has a reception slot 209 reaching from the block rear side 201 onto the block front side 202 lying opposite in a distal direction. The reception slot 209 is rectilinearly elongated parallel to the pivot axis S and/or the guide path E and has inner walls 2091, 2092 lying opposite one another in a mediolateral direction, on which the guide faces 207, 208 are arranged and/or formed. Here, the latter is the case. The reception slot furthermore has an insertion opening 2093, here arranged on the block lower side 204. The insertion opening 2093 is adapted for insertion of the bearing element 300 into the reception slot 209. The reception slot 209 furthermore has an end wall 2094. The end wall 2094 lies opposite the insertion opening 2093 in an anterior direction along the pivot axis S. The end wall 2094 forms a stop for the bearing element 300, or more precisely: its upper side 304 (see FIG. 7).

Figure 6:
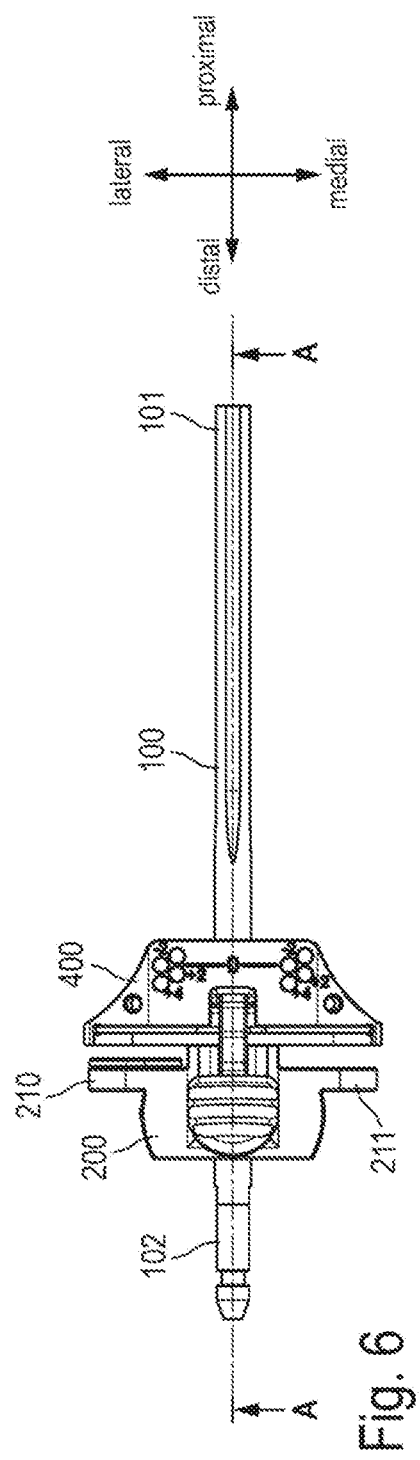
FIG. 6 shows the surgical instrument system according to FIGS. 1 to 5 in a schematic plan view with a posteriorly directed viewing direction.
Figure 7:
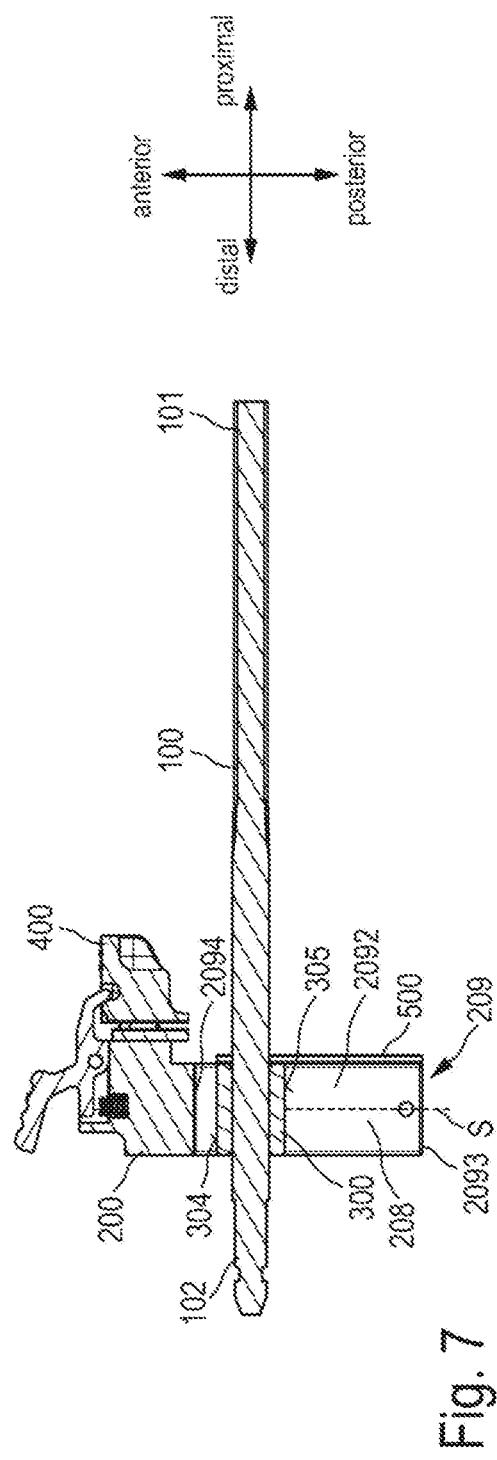
FIG. 7 shows a schematic longitudinal sectional view along a section line A-A according to FIG. 6.

In the embodiment shown, the reception slot 209 subdivides the reference block 200 into a lateral block section 201 and a medial block section 211 (see in particular FIG. 6). Accordingly, the block rear side 201 is subdivided into a lateral block rear side and a medial block rear side (both without reference signs).

Figure 8:
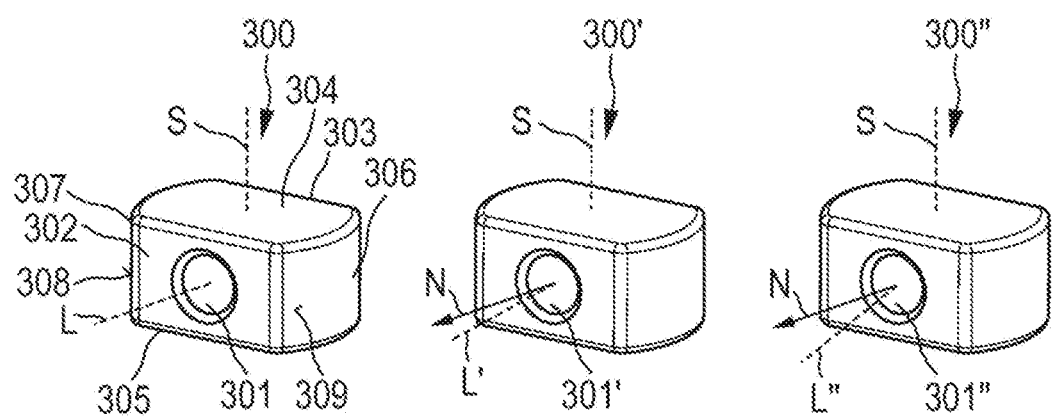
FIG. 8 shows a schematic perspective view of different bearing elements with differently inclined reception bores.
Figure 9:
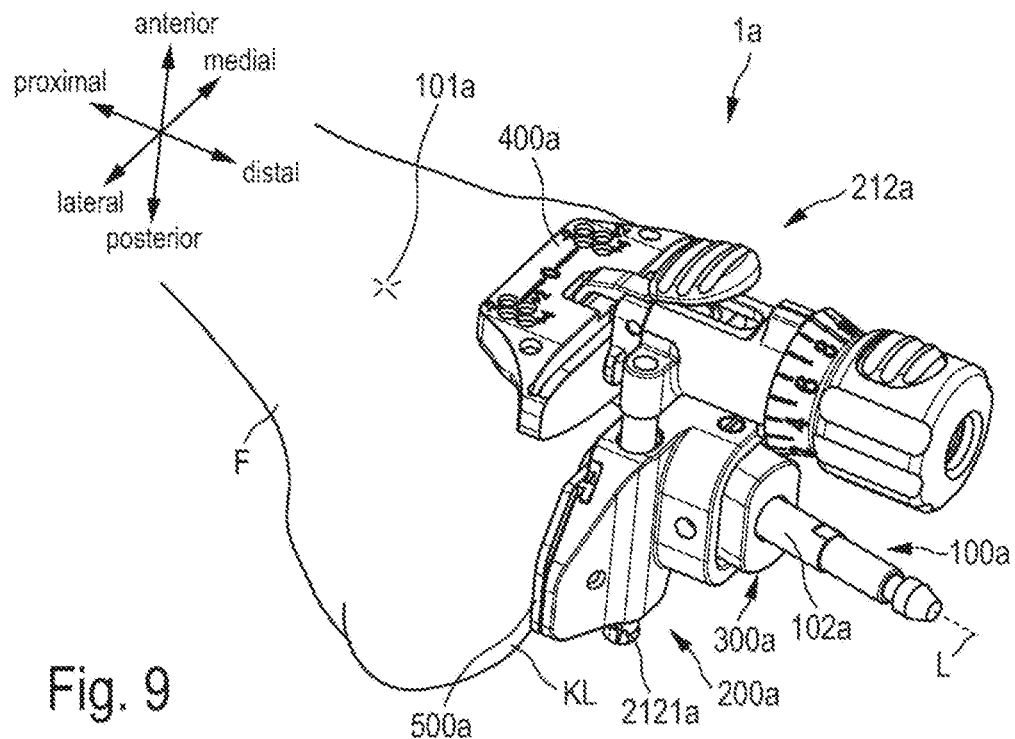
FIG. 9 shows a schematic perspective view of another embodiment of a surgical instrument system according to the present disclosure in an intraoperative situation.
Figure 10:
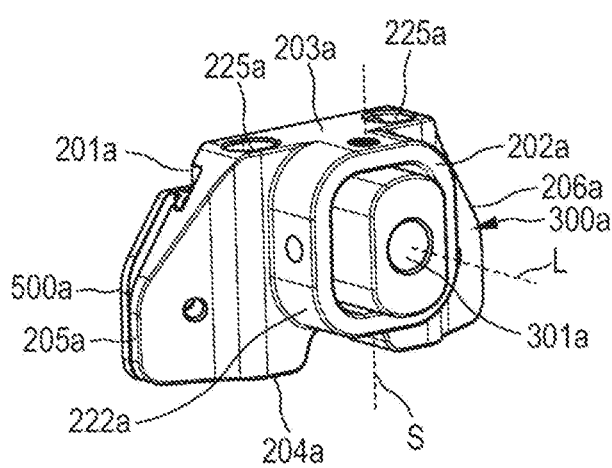
FIG. 10 shows a schematic perspective view of the reference block and the bearing element of the surgical instrument system according to FIG. 9.
Figure 11:
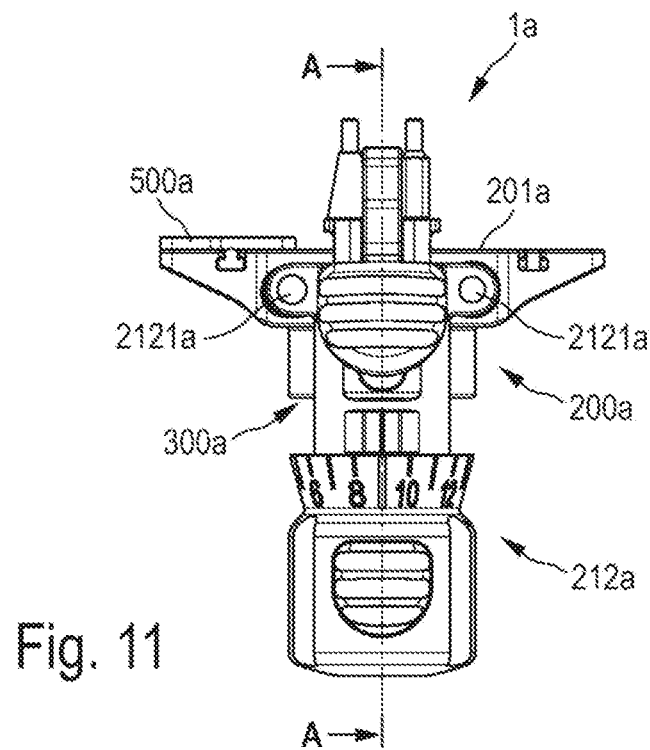
FIG. 11 shows the surgical instrument system according to FIG. 9 in a schematic plan view with a posteriorly directed viewing direction.
Figure 12:
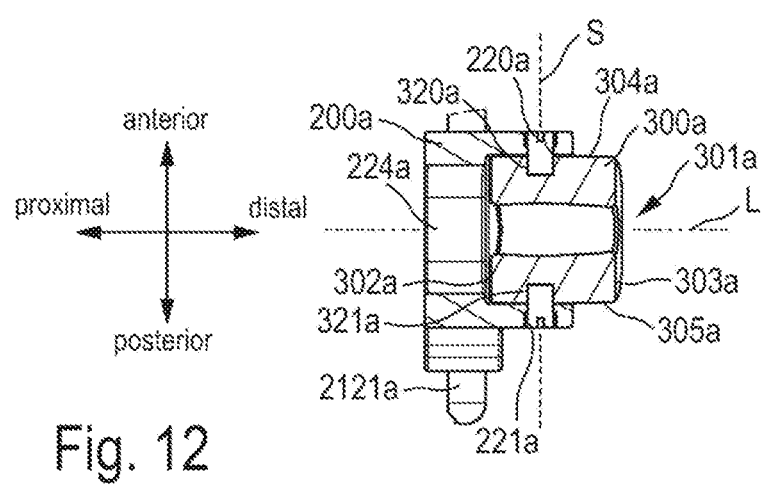
FIG. 12 shows a schematic longitudinal sectional view along a section line A-A according to FIG. 11.
Figure 13:
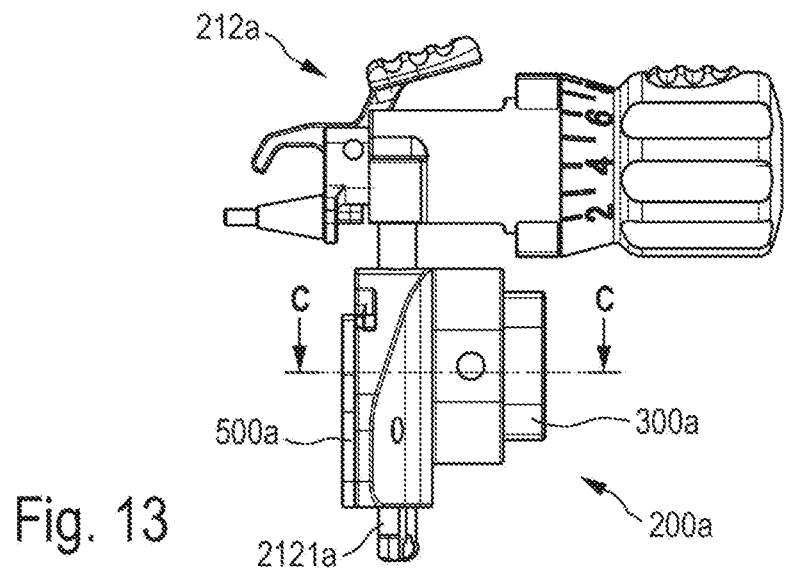
FIG. 13 shows the surgical instrument system according to FIGS. 9 to 12 in a schematic side view with a medially directed viewing direction.

As may be seen with the aid of FIG. 8, the surgical instrument system 1 in the present case has a plurality of different bearing elements 300, 300', 300". These may also be referred to as a first bearing element 300, second bearing element 300' and third bearing element 300". The bearing elements 300, 300', 300" have a substantially identical configuration and functionality, and differ only with regard to the alignment of the longitudinal axis L, L', L" of the respective reception bore 301, 301', 301". The longitudinal axes L, L', L" are each elongated with a different inclination.

The different inclination angles are illustrated in relation to a normal direction N of the block rear side 201. The normal direction N is indicated in FIG. 8 by way of example for the second bearing element 300' and the third bearing element 300". In the case of the first bearing element 300, the normal direction N coincides with the longitudinal axis L. The bearing elements 300, 300', 300" can each be mounted mutually interchangeably on the reference block 200.

Figure 2:
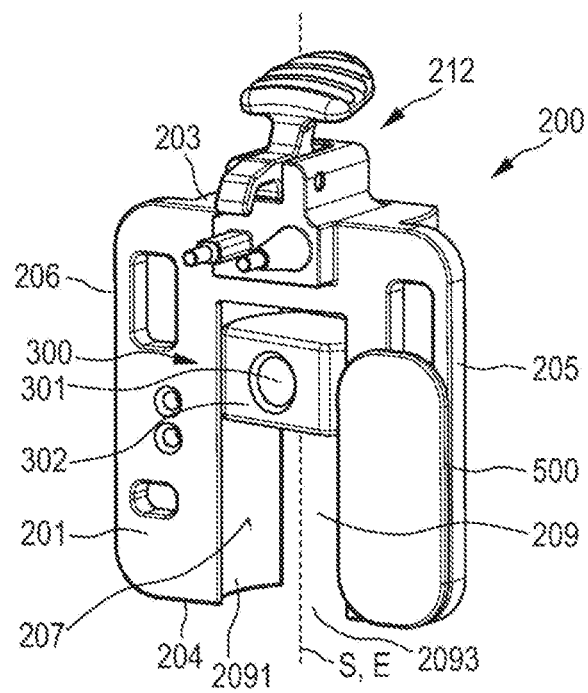
FIG. 2 shows a schematic perspective view of the reference block and the bearing element of the surgical instrument system according to FIG. 1 in a viewing direction directed onto the block rear side.

For the purpose of disassembly, the bearing element 300—starting from the configuration shown in FIG. 2—can be pulled out of the reception slot 209 in a posterior direction. Assembly is carried out kinematically in the reverse way. The differently inclined longitudinal axes L, L', L" may selectively be positioned at different inclination angles in relation to the femur F. In particular, the so-called flexion-extension angle can in this way be adapted simply and precisely. The longitudinal axes L, L', L" differ from one another in set angular increments. Consequently, the adaptation of the angular alignment of the reference block 200 can be carried out in set defined increments. The adjustment of the inclination of the reference block 200 is in this case carried out about an axis aligned in a mediolateral direction, which intersects both the pivot axis S and the longitudinal axis L.

In the embodiment shown, the surgical instrument system 1 furthermore has said (optional) cutting block 400. The function and configuration of the cutting block 400 are well known to a person skilled in the art in principle. The cutting block 400 is used to receive and guide a saw blade for the resection of the distal condyles of the femur F. The cutting block 400 is applied releasably on the reference block 200 by means of a fixing device 212. Details of the fixing device 212 and of the cutting block 400 are not of essential importance with regard to the present disclosure. Further explanations relating to these may therefore be omitted.

The (optional) compensation element 500 is adapted to compensate for a wear (not represented in detail) of the lateral distal condyle KL, and for this purpose is secured releasably on the block rear side 201. The compensation element has a proximodistal thickness (not denoted in detail), which corresponds approximately to the amount of said wear of the lateral condyle KL. In order to compensate for different amounts of wear, the surgical instrument system 1 in the present case has a plurality of different compensation elements 500, 500', 500" (see FIG. 4). Merely for graphical reasons, only the compensation element 500 represented in detail. The compensation elements 500, 500', 500" have different proximodistal thicknesses and can be applied mutually interchangeably on the block rear side 201. The compensation elements 500, 500', 500" and their application on the block rear side 201 are not essential with regard to the present disclosure. Further explanations relating to these may therefore be omitted.

In the embodiment shown, the intramedullary rod 100 has a length of 175 mm. In some embodiments, which are not shown in the drawings, the length is between 120 mm and 250 mm.

FIGS. 9 to 14 show another embodiment of a surgical instrument system 1a according to the present disclosure. The functionality and configuration thereof are substantially identical to the surgical instrument system 1 according to FIGS. 1 to 7. In order to avoid repetition, only the essential differences of the surgical instrument system 1a from the surgical instrument system 1 according to FIGS. 1 to 7 will primarily be discussed below. Component parts and/or sections that are functionally equivalent are denoted by identical reference numbers with the addition of the lowercase letter "a". Component parts and/or sections that are functionally equivalent will not be explained separately. Instead, mention of and explicit reference to the comments relating to the surgical instrument system 1 will be made.

The surgical instrument system 1a differs primarily by a different implementation of the pivotability between the reference block 200a and the bearing element 300a. For the purpose of pivotable mounting, in the present case an axial guide is provided. The axial guide has axial elements 220a, 221a oriented coaxially with the pivot axis S and corresponding axial recesses 320a, 321a (see in particular FIG. 12). In the present case, the axial elements 220a, 221a are assigned to the reference block 200a. The axial recesses 320a, 321a are arranged and/or formed on the bearing element 300a.

The axial elements 220a, 221a are aligned coaxially with one another. The same applies correspondingly for the axial recesses 320a, 321a. The axial elements 220a, 221a and the axial recesses 320a, 321a cooperate in gliding movement about the pivot axis S. For this purpose, one of the axial elements 220a, 221a in each case engages axially in one of the axial recesses 320a, 321a. Both the axial elements 220a, 221a and the axial recesses 320a, 321a are in the present case aligned orthogonally to the longitudinal axis of the reception bore 301a.

In relation to the longitudinal axis L, the terms anterior axial element 220a and posterior axial element 221a may also be used in the present case. This also applies, mutatis mutandis, to the axial recesses 320a, 321a.

The anterior axial recess 320a is sunk in a posterior direction into an upper side 304a of the bearing element 300a. The posterior axial recess 321a is sunk in an anterior direction into a lower side 305a of the bearing element 301a. The two axial recesses 320a, 321a are each introduced in the form of a blind bore into the bearing element 300a.

The axial elements 220a, 221a are each secured releasably on the reference block 200a, and in the present case each screwed in the form of a countersunk screw to a screw thread suitable therefor of the reference block 200a. In order to release the axial elements 220a, 221a, they are each equipped with a tool face (without reference sign) for receiving a complementary tool.

Figure 14:
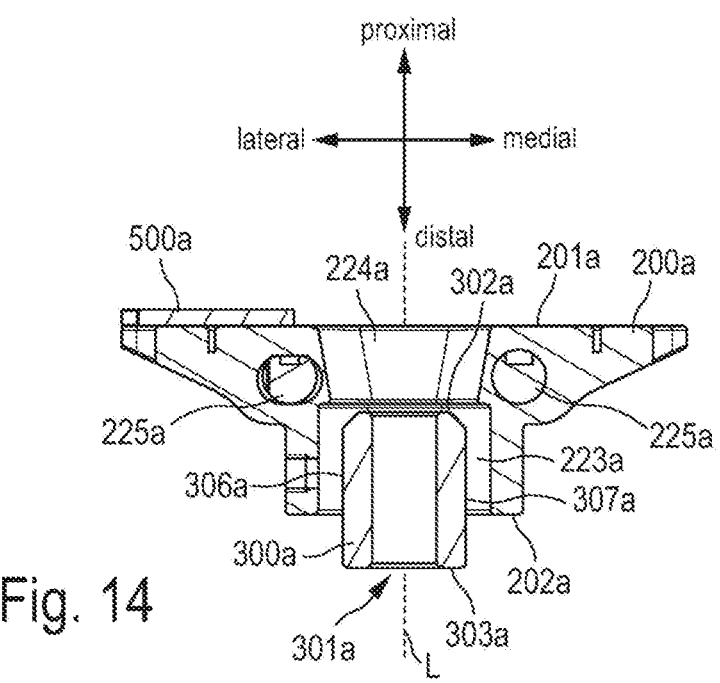
FIG. 14 shows a schematic longitudinal sectional view along a section line C-C according to FIG. 13.

In the embodiment shown, the bearing element 300a is mounted in a hollow-cylindrical projection 222a of the reference block 200a. The projection 222a has a reception notch 223a (FIG. 14), in which the bearing element 300a is pivotably mounted in the manner described above. The reception notch 223a opens in a proximal direction into a hole 224a (FIG. 14). The hole 224a is used to receive the distal rod end 102a, which can be guided starting from the block rear side 201a through the hole 224a and from there via the reception bore 301a further through the reference block 200a.

In contrast to the bearing element 300 of the surgical instrument system 1, the bearing element 300a is not mounted linearly displaceably in an anteroposterior direction along the pivot axis S on the reference block 200a.

In order nevertheless to allow anteroposterior adjustability of the cutting block 400a, the fixing device 212a is correspondingly displaceable relative to the reference block 200a. For this purpose, the reference block 200a has guide bores 225a (FIG. 10), in which guide pegs 2121a of the fixing device 212a axially engage.

In other regards, the rest of the functionality and configuration of the fixing device 212a are not essential with regard to the present disclosure, so that further explanations relating to these can be omitted.

In relation to the functionality of the compensation element 500*a*, the comments relating to the surgical instrument system 1 apply accordingly. Furthermore, a plurality of different compensation elements having a different proximodistal thickness may again be provided.

Referring to FIG. 8, the surgical instrument system 1*a* may again have a plurality of different bearing elements having differently inclined longitudinal axes, which can be mounted mutually interchangeably on the reference block 200*a*. In order to change the bearing elements, the axial elements may be released from the reference block 200*a* and re-fastened. This by means of the screw connection described above.

The invention claimed is:

1. A surgical instrument system for use in a total knee arthroplasty, the surgical instrument system comprising:
   an intramedullary rod that is elongated between a proximal rod end and a distal rod end and is adapted for introduction into a medullary space of a femur;
   a reference block that is slidable onto the distal rod end, the reference block comprising a block rear side oriented in a proximal direction, the block rear side adapted to bear on distal condyles of the femur; and
   a plurality of bearing elements,
   the reference block being mounted or mountable on the distal rod end by one of the bearing elements,
   the reference block having a gliding guide with guide faces that are concavely curved in the shape of a circle arc and lie opposite one another in a mediolateral direction,
   each bearing element having gliding faces that are convexly curved in the shape of a circle arc and lie opposite one another in the mediolateral direction,
   the gliding faces configured to glide in rotation about a pivot axis in an anteroposterior direction and cooperating form-fittingly with the guide faces in a proximodistal and mediolateral direction,
   each bearing element having a reception bore for coaxial and radially form-fit reception of the distal rod end,
   each bearing element being releasably mountable on the reference block so as to be pivotable relative to the reference block at least about the pivot axis,
   the plurality of bearing elements comprising at least a first bearing element and a second bearing element,
   the reception bore of the first bearing element having a first angle of inclination relative to a direction normal to the block rear side when mounted on the reference block, and
   the reception bore of the second bearing element having a second angle of inclination relative to the direction normal to the block rear side when mounted on the reference block, the second angle of inclination being different from the first angle of inclination,
   the first bearing element being selectively mountable on the reference block to connect the intramedullary rod to the reference block at a first angle relative to the block rear side, and
   the second bearing element being selectively mountable on the reference block to connect the intramedullary rod to the reference block at a second angle relative to the block rear side that is different from the first angle relative to the block rear side.

2. The surgical instrument system according to claim 1, wherein:
   the first angle of inclination is 0 degrees; and
   the second angle of inclination is greater than 0 degrees.

3. The surgical instrument system according to claim 1, wherein the guide faces are each rectilinearly elongated parallel to the pivot axis, the gliding faces cooperating along the pivot axis in translational gliding movement with the guide faces.

4. The surgical instrument system according to claim 1, wherein the reference block has a reception slot that reaches from the block rear side onto a block front side lying opposite in a distal direction and is rectilinearly elongated parallel to the pivot axis and has inner walls, which lie opposite one another in a mediolateral direction and on which the guide faces are arranged and/or formed, the reception slot having an insertion opening arranged anteriorly on a block upper side or posteriorly on a block lower side of the reference block for insertion of one of the bearing elements.

5. The surgical instrument system according to claim 1, wherein the reference block has an axial guide with at least one axial element oriented coaxially with the pivot axis, each bearing element having at least one axial recess oriented coaxially with the pivot axis, the at least one axial element engaging in the at least one axial recess in such a way that the at least one axial element is configured to glide about the pivot axis.

6. The surgical instrument system according to claim 1, further comprising a plurality of different compensation elements having different proximodistal thicknesses, the plurality of different compensation elements configured for being applied mutually interchangeably on the block rear side to compensate for a differently pronounced wearing of distal condyles.

7. The surgical instrument system according to claim 1, further comprising a cutting block adapted for cut guiding on distal condyles of the femur, the cutting block releasably fixed or fixable on a fixing device of the reference block.

8. The surgical instrument system according to claim 1, wherein the intramedullary rod has a length of between 120 mm and 250 mm.

* * * * *